(12) United States Patent
Lee et al.

(10) Patent No.: US 6,437,102 B1
(45) Date of Patent: Aug. 20, 2002

(54) METHOD OF SEPARATING PRIONS FROM BIOLOGICAL MATERIALS

(75) Inventors: Douglas C. Lee, Apex; Steve R. Petteway; Christopher J. Stenland, both of Cary, all of NC (US)

(73) Assignee: Bayer Corporation, Pittsburgh, PA (US)

( * ) Notice: Subject to any disclaimer, the term of this patent is extended or adjusted under 35 U.S.C. 154(b) by 0 days.

(21) Appl. No.: 09/638,275

(22) Filed: Aug. 14, 2000

Related U.S. Application Data

(63) Continuation of application No. 09/448,771, filed on Nov. 24, 1999, now abandoned.

(51) Int. Cl.$^7$ .............................. A23J 1/00; C07K 1/00; G01N 33/53
(52) U.S. Cl. ..................... 530/412; 530/422; 435/7.1; 435/975; 435/962
(58) Field of Search ................................. 435/975, 962, 435/7.1; 530/412, 422

(56) References Cited

U.S. PATENT DOCUMENTS

| | | | |
|---|---|---|---|
| 4,115,375 A | * | 9/1978 | Pedersen ................ 260/112 R |
| 5,633,349 A | | 5/1997 | Reichl ..................... 530/364 |
| 5,737,061 A | | 4/1998 | Sinclair et al. ............. 351/246 |
| 5,750,361 A | | 5/1998 | Prusiner et al. ............. 435/23 |
| 5,756,678 A | | 5/1998 | Shenoy et al. ............... 530/356 |
| 5,773,572 A | | 6/1998 | Fishleigh et al. ............ 530/324 |
| 5,792,901 A | | 8/1998 | Prusiner et al. ................ 800/2 |
| 5,808,011 A | | 9/1998 | Gawryl et al. ............... 530/416 |
| 5,834,593 A | | 11/1998 | Prusiner et al. ............. 530/350 |
| 5,846,533 A | | 12/1998 | Prusiner et al. .......... 424/130.1 |
| 5,908,969 A | | 6/1999 | Prusiner et al. ................ 800/4 |
| 6,150,172 A | * | 11/2000 | Schmerr et al. ............ 435/975 |

OTHER PUBLICATIONS

Turk et al. Eurpean Journal of Biochemistry, vol. 176, pp. 21–30, 1988.*

* cited by examiner

*Primary Examiner*—Jezia Riley
(74) *Attorney, Agent, or Firm*—Womble Carlyle Sandridge & Rice, PLLC; Carl B. Massey, Jr.

(57) ABSTRACT

Disclosed is a method for separating prions from biological materials. The method includes adding a polyalkylene glycol, such as polyethylene glycol, to a solution of the biological material such that a precipitate containing the prion is formed. This precipitate is then separated from the solution of biological material, thereby removing prions. Biological materials include biologically derived fluids, such as cerebrospinal fluid, biological samples, such as brain homogenates, blood plasma fractions, and aqueous solutions of recombinantly produced products. The disclosed method provides an effective process for the removal of these infectious materials from the biological materials, which may be further processed to provide the therapeutic compositions.

41 Claims, No Drawings

METHOD OF SEPARATING PRIONS FROM BIOLOGICAL MATERIALS

CROSS-REFERENCE TO RELATED APPLICATIONS

This application is a continuation of U.S. patent application Ser. No. 09/448,771, filed Nov. 24, 1999, now abandoned.

FIELD OF THE INVENTION

The invention relates to the separation of transmissible spongiform encephalopathies (TSEs), or prions, from biological materials. The prions are separated from biological materials by precipitation with a polyalkylene glycol, such as polyethylene glycol.

BACKGROUND

Transmissible spongiform encephalopathies (TSEs), or pathogenic prions, cause fatal neurodegenerative diseases in humans and other mammalian species, particularly sheep, goats, cattle, mink, elk, and deer. The human forms of the disease include Creutzfeldt-Jakob disease (CJD), Gerstmann-Sträussler-Scheinker (GSS) syndrome, fatal familial insomnia (FFI), and Kuru. Symptoms of these diseases include myoclonus, ataxia, and progressive dementia. The pathology of these diseases includes the formation of amyloid plaques in the brain.

The occurrence of prion diseases has been linked to infectious transmission, as well as genetic and sporadic, causes. For example, Kuru, which afflicted the Fore tribe of New Guinea, was caused by the ingestion of infected brain tissue of other tribal members during ritualistic cannibalism. Alpers (1979) *Slow Transmissible Diseases of the Nervous System,* Vol. 1, S. B. Pruisner and W. J. Hadlow, eds. (New York: Academic Press), pp. 66–90. More recently, the occurrence of variant CJD in the United Kingdom has been postulated to be the result of consumption of beef from cattle infected with a TSE. G. Chazot, et al., (1996) *Lancet* 347:1181; R. G. Will, et al., (1996) *Lancet* 347:921–25. Similarly, iatrogenic CJD has been caused by the injection of human growth hormone derived from cadaveric pituitaries. Brown, et al., (1992) *Lancet* 340:24–27. Instances of infectious activity of prions, as noted above, suggest that prion infectivity may be transmitted through biological materials.

Prions are believed to infect humans and other mammals via transmission of a protein, the prion protein, without concomitant transmission of a nucleic acid. It has been postulated that the infectious agent is a disease-causing variant of the naturally-occurring, cellular prion protein ($PrP^C$), the physiologic function of which is presently not known. In this theory, the variant form of the prion protein ($PrP^{Sc}$) induces structural changes in the normal form of the prion protein ($PrP^C$), thereby converting it to the disease-causing form of the protein ($PrP^{Sc}$).

Therapeutic compositions are often derived from biological materials. For example, therapeutically valuable proteins such as Factor VIII, α-l proteinase inhibitor, and albumin are isolated from human plasma. Other infectious agents, such as human immunodeficiency virus (HIV) and hepatitis C virus (HCV) have been known to be transmitted by therapeutic use of blood or blood products that have not undergone inactivation methods or procedures that effectively remove the agents from the product processing stream. Evidence of the transmission of TSEs through other biological materials raises concern over possible transmission of TSEs through blood and blood-derived products, recombinant products, and other products of biological orgin.

Known methods for reducing the risk of infection from blood borne pathogens, such as HIV and HCV, however, are not effective at inactivating prions. Furthermore, methods that do reduce the risk of infection from prions, which include treatment with strong base and/or autoclaving, are not suited for use with procedures for the preparation of therapeutic proteins, because such procedures denature the proteins.

A method for separating prions from biological materials, such as blood plasma fractions and aqueous solutions of recombinantly produced proteins, is therefore needed. The present invention provides a method of separating prions from such biological materials without denaturing therapeutically valuable proteins.

SUMMARY OF THE INVENTION

The invention provides methods for the separation of prions from biological materials. Biological materials include biologically derived fluids, such as blood plasma fractions, biological samples, such as samples of tissues, and aqueous solutions of recombinantly produced products, such as recombinant proteins. Generally, the methods provide for the separation of prions from the biological material by adding a polyalkylene glycol to the biological material to obtain a mixture of the polyalkylene glycol and the biological material. From this mixture a precipitate containing the prion is formed. This precipitate is separated from the mixture, such as by filtration or centrifugation, to obtain a purified biological material.

The polyalkylene glycol for use in methods of the invention may be polyethylene glycol (PEG) or polypropylene glycol (PPG), but PEG is preferred. The PEG is added to the biological material so that the weight of PEG per volume of the resulting mixture is at least about 2%. The weight of PEG per volume of resulting mixture is preferably about 3% to about 15%, and is more preferably greater than or equal to about 10%. The PEG for use in methods of the invention has a molecular weight of between about 2,000 and about 10,000, and preferably has a molecular weight of about 3,350.

The method of the invention may be used to separate prions from blood plasma fractions. When used to separate prions from blood plasma fractions. the method of the invention results in at least 3 logs of clearance of prions from the blood plasma fraction.

The method of the invention may be used to separate prions from aqueous solutions of recombinantly produced products. A recombinantly produced product may be a recombinantly produced protein.

In preferred methods of the invention, a prion is removed from a blood plasma fraction including the prion by adding PEG to the blood plasma fraction so that the mixture obtained is at least about 10% weight per volume PEG. From this mixture, the prion is precipitated. The precipitate, including the prion, is then separated from the mixture. In this embodiment, the PEG preferably has a molecular weight of about 3,350 and is preferably 11.5% weight per volume of the resulting mixture.

The present invention therefore provides methods for the separation of prions from biological materials, such as blood plasma fractions, without using harsh conditions that often denature therapeutically valuable proteins. Such methods reduce the risk of transmission of these infectious prions from biological materials, which are then further processed for therapeutic use. These and other aspects of the invention will be more apparent from the following description and claims.

DETAILED DESCRIPTION

Methods of the invention provide for the separation of prions from biological materials, such as biologically derived fluids, biological samples, blood plasma fractions, and solutions of recombinantly produced products, such as proteins. Methods of the invention provide for the precipitation of prions from the biological material by adding a polyalkylene glycol, such as polyethylene glycol (PEG), to the biological material. The precipitate containing the prions is then separated from the biological material, such as by filtration or centrifugation, for example.

PEG for use in methods of the invention has a molecular weight of between about 2,000 and about 10,000, and preferably has a molecular weight of about 3,350. The PEG is added to the biological material so that the weight of PEG per volume of the resulting mixture is at least about 2%. The PEG is preferably between about 3% and about 15% of the resulting mixture, and is more preferably greater than or equal to about 10%.

As described above, the biological material for use in methods of the invention may be a biologically derived fluid, a biological sample, a blood plasma fraction, or a solution of a recombinantly produced product. A biologically derived fluid includes, but is not limited to, solutions derived from biological materials, and body fluids, such as cerebrospinal fluid, lymphatic fluid, plasma, etc. A biological sample includes, but is not limited to, body tissues and solutions of body tissues, such as central nervous system tissue (e.g., brain), spleen, tonsils, etc. Such solutions preferably do not contain a detergent. Blood plasma fractions include any portion or all of plasma derived from the blood. Finally, a solution of a recombinantly produced product includes, but is not limited to, aqueous solutions of recombinantly produced proteins or proteins produced by transgenic animals.

The prion protein (PrP) is present in its normal, cellular form ($PrP^C$) in most biological materials, and is particularly prevalent in central nervous system (CNS) tissue. The physiological function of $PrP^C$ is, however, not known. In theory, $PrP^C$ undergoes a conformational change in the diseased state. Evidence for this theory is the presence of amyloid plaques containing an abnormally folded form of PrP in the brains of TSE victims. This conformational change alters the physicochemical properties of the protein, thereby rendering it less soluble in physiological fluids and more proteinase resistant. This altered form of the protein is typically designated $PrP^{Sc}$ (prion protein scrapie) and is believed to be the infectious agent, or, at least, necessary for infection. Removal of $PrP^{Sc}$ from biological materials may,, therefore, decrease the risk of transmission of TSEs.

A correlation between use of infected biological samples or biologically derived fluids and the transmission of prion disease has been demonstrated. For example, prion diseases have been transmitted through therapeutic use of infected body tissues, such as corneas, and biologically derived fluids, such as solutions of human growth hormone derived from cadaveric pituitaries. These concerns over the risk of transmission of prion disease through the use of biological materials can be addressed by the methods of the invention, as shown in the examples below.

EXAMPLE 1

A correlation between the presence of $PrP^{Sc}$ in a blood plasma fraction and infectivity of the blood plasma fraction has been shown. Blood plasma fractions spiked with the prion protein from infected hamster brains were treated according to methods of the invention in order to remove the prions. Some blood plasma fractions infected with the prion protein were left untreated. Additionally, a control fraction treated with uninfected hamster brains was prepared. Treated, untreated, and control blood plasma fractions were administered to test animals to measure the levels of TSE infectivity. The test animals were held and observed for signs of disease, and after sacrifice, their brains were examined for TSE pathology. Additionally, a Western blot assay was used to determine the presence of $PrP^{Sc}$ in the blood plasma fractions. Compared with the results from the animal testing, this assay showed a correlation between removal of $PrP^{Sc}$ and reduced infectivity titer and thereby proved to be a reliable indicator of whether the risk of infection from prions in blood plasma fractions was reduced. These procedures are discussed in more detail below.

Preparation of Infected Blood Plasma or Plasma Fractions

To determine a correlation between infectivity and the presence of $PrP^{Sc}$ in blood plasma fractions, blood plasma samples or fractions thereof were first spiked with prions. The source of the infection was 10% hamster brain homogenates prepared with tissues infected with the 263 K hamster-adapted scrapie agent. (Kimberlin, et al., 1977, *Journal of General Virology*, 34:395–304.)

The homogenates were used to infect various blood plasma fractions with the scrapie agent. In this example, the Fraction IV-1 paste from the Cohn-Oncley fractionation procedure was suspended in distilled $H_2O$ and NaCl added to a concentration of 110 mM at pH 8.0 at 4.0° C. (For the Cohn-Oncley fractionation procedure see E. J. Cohn, et al., *J. Amer. Chem. Soc.*, 68, 459 (1946); E. J. Cohn, U.S. Pat. No. 2,390,074; and Oncley, et al., *J. Amer. Chem. Soc.*, 71, 541 (1949).) The suspended paste (final volume of 20 ml) was spiked to a final concentration of 1% infected brain homogenate with the 10% solution of brain homogenate described above. The mixture was stirred for 10 minutes, and an 11 ml prove sample removed for later analysis.

Removal of Prions from Infected Blood Plasma and/or Plasma Fractions

The infected blood plasma samples or fractions thereof were then treated using methods of the invention to remove $PrP^{Sc}$. To the spiked suspension of Fraction IV-1 paste was incrementally added PEG-3350 (Union Carbide, Danbury, Conn.) as a solid over 15 minutes to yield a final solution of 11.5% PEG (w/w). The resulting mixture was stirred for 30 at 4.0° C. The pH was then lowered to 5.15 with the addition of 1 N acetic acid. The solution was then centrifuged at 5000×g at 4.0° C. for 5 min. The supernatant was filtered through a 0.8 μm filter (Millipore, Boston, Mass.) and the pH of the clarified filtrate adjusted to 6.05 by the addition of 1 N NaOH. The paste was resuspended in an equal volume of 0.1% bovine serum albumin (BSA, Sigma Chemical Co, St. Louis, Mo.) in phosphate buffered saline (PBS, Sigma Chemical Co, St. Louis, Mo.) and stored at 4° C. until later use.

Animal Testing to Confirm Removal of Prions from Blood Plasma

To determine the partitioning of infectivity during fractionation, putatively infected and non-infected samples derived from the methods of invention were inoculated intracerebrally into male Golden Syrian hamsters using a standard rodent bioassay to estimate infectivity. (Kimberlin, et al., 1977, *Journal of General Virology*, 34:395–304.)

The inoculated hamsters were monitored for signs of scrapie. As control samples, a solution of 10% SBH in Hank's balanced salt solution (HBSS; Sigma Chemical Co, St. Louis, Mo.) was serially diluted in 1.0 log increments to $10^{-9}$ with HBSS. Each dilution was given to a group of six hamsters in 50 µl portions. Another group of six hamsters received HBSS only.

The spiked blood plasma fraction and the resulting fractions treated by methods of the invention (i.e., those treated with PEG) were also administered to hamsters. The paste obtained from the procedure of prion removal described above was resuspended and serially diluted in seven single log increments. A 50 µl portion of each dilution was administered to a group of six hamsters. The prove sample of the spiked material, noted above, was administered to another group of hamsters as an undiluted sample.

The animals were held and observed for signs of disease. Animals showing signs of disease were sacrificed and thin sections of brain tissue examined for the scrapie pathology, including vacuolized brain lesions. Animals that died or were sacrificed without showing signs of disease were subjected to complete necropsy.

Western Blot Assay

A Western blot assay to detect the presence of $PrP^{Sc}$ was performed on both blood plasma samples and samples of brain tissue from animals inoculated with infected blood plasma samples. The Western blot assay was performed according to Lee, et al., *Journal of Virological Methods* (in press), which is hereby incorporated by reference in its entirety. Modifications to the assay disclosed in Lee, et al. included either a 1:10,000 dilution of the secondary antibody obtained from Biosource International (Camarillo, Calif., Cat. No. AMI04405 or AMI3405) or a 1:15,000 dilution of the secondary antibody obtained from Southern Biotechnology Associates (Birmingham, Ala., Cat. No. 1080-04). Additionally, all samples analyzed by the Western blot assay were pre-treated with proteinase K (PK; Boehringer Mannheim, Indianapolis, Ind.) to eliminate $PrP^{C}$, which is digested by this procedure. In addition, the PK treatment converts $PrP^{Sc}$ to a more protease-resistant form of the prion protein, $PrP^{RES}$, which migrates in the Western blot assay with the characteristic triplet banding pattern resulting from its variable glycosylation sites.

Sample preparation was performed using a high sensitivity sample preparation protocol (Lee, et al., supra). In this method, 1 ml of each of the undiluted samples from the fractionation procedure were treated with 4 $\mu$M PK (37° C. for 1 hour) followed by incubation with 4 mM 4-(2-aminoethyl) benzenesulfonyl fluoride (ABESF, Boehringer Mannheim, Indianapolis, Ind.). Next, the samples were centrifuged at 20,000×g for one hour at 4° C. in a fixed angle rotor. The supernatants were discarded and the pellets were resuspended in 80 $\mu$l of 2×SDS-PAGE sample buffer. After heating, each sample was serially diluted in 0.5 log increments on a 100 $\mu$l scale using 1×SDS-PAGE sample buffer as the diluent, then loaded on SDS-PAGE gels. The remainder of the assay was performed as described in Lee, et al., supra.

Results

The Western blot assay proved to be a reliable indicator of the risk of infectivity from blood plasma fractions spiked with $PrP^{Sc}$, and the precipitation of prions with PEG proved to be a reliable method of removing infectious TSEs from blood plasma fractions. The concentration of PEG has an effect on the precipitation of prion protein from the spiked blood plasma fractions. In these studies PEG was added from 3% to 10% and the effluents were monitored for the prion protein using the Western blot assay. The data demonstrate effective removal of $PrP^{Sc}$ at increasing PEG concentrations. While some prion protein remains in the blood plasma fraction at 4% PEG (w/w), greater portions of the prion protein are removed from the blood plasma fraction with increasing PEG concentrations. At 10% PEG, the $PrP^{Sc}$ is virtually absent from the blood plasma fraction.

Those blood plasma fraction samples that had prions spiked into the input solution were precipitated by addition of PEG showed, on average, ≧4.9 logs of clearance of prions compared to fractions that had not undergone PEG precipitation. Additionally, the Western blot data correlated with the infectivity data. Those samples that were shown by Western blot to be clear of $PrP^{Sc}$ also did not produce infection in test animals. The data of both Western blot and bioassay results are presented in Table 1.

TABLE 1

| | Input | | Effluent | | Paste | | Difference of Effluent from Input (Clearance) | |
|---|---|---|---|---|---|---|---|---|
| Fraction IV-1 Paste (11.5% PEG) | 4.9 | 9.9* | 0.1 | ≦2.4 | 4.0 | 7.9 | ≧4.1 | 7.5 |

The data are in log units of prion detection (left column) or infectivity (right column).
*The bioassay data for this sample was estimated from the titer of the original spiking material.

EXAMPLE 2

As described above, TSEs may be transmitted by infected biological samples, such as tissue samples, brain homogenates, etc. The invention further relates to the removal of prions from tissue samples. According to methods of the invention, a detergent is not needed in order to precipitate prions from biological samples with PEG.

Ten percent scrapie infected brain homogenate from 263K infected hamsters is prepared in a Dounce homogenizer. One gram of thawed brain tissue is placed into the mortar and 9 ml of ice cold Tris-buffered saline (TBS) is added. The Dounce pestle is pushed through the sample 20 times to generate the homogenate. The homogenate is carefully aspirated leaving the large particulate behind in the Dounce. The homogenate is diluted in TBS to make a 1% homogenate, and a prove sample is removed. Next PEG 3,350 is added to 3% (w/w), preferably to 10%, and allowed to mix for 30 minutes. The mixture is centrifuged in a fixed angle rotor for 5 minutes at 5000×g. The supernatant is decanted, and the precipitate is resuspended to the original volume in 0.1% BSA/PBS. These fractions are analysed by Western blot assay, as described in example 1.

Once treated with PEG, the resulting fluid fraction is expected to be reduced in prion concentration. This ensures that any biological material derived from the biological fluid is at a reduced risk for the transmission of a TSE.

EXAMPLE 3

Methods of the invention may also be used to remove prions from aqueous solutions of recombinantly or transgenically produced products, such as the protein α-1 proteinase inhibitor (α-1 PI). Such application would be similar to that described in example 1, where α-1 PI is purified from a recombinant source rather than blood plasma. The recombinant α-1 PI is contained in a fermentation broth or as an intermediate purified protein thereof. This solution is thermostated to 4 to 8° C. and PEG 3,350, in either a solid or liquid form, is added to 10% (w/w) over a period of 20–30 minutes. The solution is acidified to a pH of 5.2 to 6.0 by the addition of 1N acetic acid. The solution is stirred for 30 minutes. The mixture is centrifuged at 5000×g for 5 minutes at 4 to 8° C. The supernatant is filtered through a 0.8 μm filter. As encompassed in this example, the supernatant will contain the α-1 PI, which has been separated from the putative TSE agent by more than 4.5 logs/ml. If required, the recombinant α-1 PI protein can be further processed for final product formulation.

EXAMPLE 4

Methods of the invention may also be used to concentrate prions for analysis of biologically derived fluids, such as cerebrospinal fluid. For example, 1.0 ml of a fluid sample is mixed with 10% (w/w) PEG 3,350 and allowed to mix at room temperature for 30 minutes. The sample is then centrifuged at not less than 5,000×g for not less than 10 minutes at 21° C. The supernatant is removed and the pellet is resuspended in 100 μl of 0.1% BSA/PBS for bioassay, or sodium dodecyl sulfate/tris (Laemelli) buffer for analysis by Western blot. The resulting precipitate is an enriched source for the prion protein and allows for easier detection of the prion protein using methods, such as ELISA or Western blot.

The invention may be embodied in other specific forms without departing from the spirit or essential characteristics thereof. The foregoing examples are included by way of illustration only. Accordingly, the scope of the invention is limited only by the scope of the appended claims.

What is claimed is:

1. A method of preparing a solution containing biological material, including at least one therapeutically valuable protein, the method comprising the steps of:
    a) adding a polyalkylene glycol to said biological material to obtain a mixture of polyalkylene glycol and biological material from which a precipitate, including substantially all infectious prions present in the mixture, is formed; and
    b) separating said precipitate including the prion from the mixture to form a resulting solution,
wherein the resulting solution is substantially free of prion infectivity.

2. The method of claim 1, wherein said polyalkylene glycol is polyethylene glycol.

3. The method of claim 2, wherein said polyethylene glycol added is at least about 2% weight per volume of the mixture.

4. The method of claim 3, wherein said polyethylene glycol is added at between about 3% to about 15%.

5. The method of claim 3, wherein said polyethylene glycol added is greater than or equal to about 10%.

6. The method of claim 2, wherein said polyethylene glycol has a molecular weight of between about 2,000 and about 10,000.

7. The method of claim 6, wherein said polyethylene glycol has a molecular weight of about 3350.

8. The method of claim 1, wherein said separating step comprises filtering said precipitate from said mixture.

9. The method of claim 1, wherein said separating step comprises subjecting said mixture to centrifugation.

10. A method of preparing a blood plasma fraction, the method comprising the steps of:
    a) adding a polyalkylene glycol to said blood plasma fraction to obtain a mixture of polyalkylene glycol and blood plasma fraction from which a precipitate, including substantially all infectious prions present in the mixture, is formed; and
    b) separating said precipitate from the mixture to form a resulting blood plasma fraction,
wherein the resulting blood plasma fraction is substantially free of prion infectivity.

11. The method of claim 10, wherein said polyalkylene glycol is polyethylene glycol.

12. The method of claim 11, wherein said polyethylene glycol added is at least about 2% weight per volume of the mixture.

13. The method of claim 12, wherein said polyethylene glycol is added at between about 3% to about 15%.

14. The method of claim 12, wherein said polyethylene glycol added is greater than or equal to about 10%.

15. The method of claim 11, wherein said polyethylene glycol has a molecular weight of between about 2,000 and about 10,000.

16. The method of claim 15, wherein said polyethylene glycol has a molecular weight of about 3350.

17. The method of claim 10, wherein said separating step comprises filtering said precipitate from said mixture.

18. The method of claim 10, wherein said separating step comprises subjecting said mixture to centrifugation.

19. The method of claim 10, wherein said separating step results in at least 3 logs clearance of prions from said blood plasma fraction.

20. A method of preparing an aqueous solution comprising a product of a recombinant process, the method comprising the steps of:
    a) adding a polyalkylene glycol to said aqueous solution to obtain a mixture of polyalkylene glycol and blood plasma fraction from which a precipitate, including substantially all infectious prions present in the mixture, is formed; and
    b) separating said precipitate from the mixture to form a resulting aqueous solution,
wherein the resulting aqueous solution is substantially free of prion infectivity.

21. The method of claim 20, wherein the product is a recombinantly produced protein.

22. The method of claim 20, wherein said polyalkylene glycol is polyethylene glycol.

23. The method of claim 22, wherein said polyethylene glycol added is at least about 2% weight per volume of the mixture.

24. The method of claim 23, wherein said polyethylene glycol is added at between about 3% to about 15%.

25. The method of claim 23, wherein said polyethylene glycol added is greater than or equal to about 10%.

26. The method of claim 22, wherein said polyethylene glycol has a molecular weight of between about 2,000 and about 10,000.

27. The method of claim 26, wherein said polyethylene glycol has a molecular weight of about 3350.

28. The method of claim 20, wherein said separating step comprises filtering said precipitate from said mixture.

29. The method of claim 20, wherein said separating step comprises subjecting said mixture to centrifugation.

30. A method of preparing a non-detergent containing biological sample, the method comprising the steps of:
    a) adding a polyalkylene glycol to said non-detergent containing biological sample to obtain a mixture of polyalkylene glycol and biological sample from which a precipitate, including substantially all infectious prions present in the mixture, is formed; and
    b) separating said precipitate from the mixture to form a resulting non-detergent containing biological sample,
wherein the resulting non-detergent containing biological sample is substantially free of prion infectivity.

31. The method of claim 30, wherein said polyalkylene glycol is polyethylene glycol.

32. The method of claim 31, wherein said polyethylene glycol added is at least about 2% weight per volume of the mixture.

33. The method of claim 32, wherein said polyethylene glycol is added at between about 3% to about 15%.

34. The method of claim 32, wherein said polyethylene glycol added is greater than or equal to about 10%.

35. The method of claim 31, wherein said polyethylene glycol has a molecular weight of between about 2,000 and about 10,000.

36. The method of claim 35, wherein said polyethylene glycol has a molecular weight of about 3350.

37. The method of claim 30, wherein said separating step comprises filtering said precipitate from said mixture.

38. The method of claim 30, wherein said separating step comprises subjecting said mixture to centrifugation.

39. A method of preparing a blood plasma fraction, the method comprising the steps of:

a) adding a polyethylene glycol to said blood plasma fraction to obtain a mixture that is at least about 10% weight polyethylene glycol, whereby a precipitate, including substantially all infectious prions present in the mixture, is formed from said mixture; and b) separating said precipitate from the mixture to formed a resulting blood plasma fraction, wherein the resulting blood plasma fraction is substantially free of prion infectivity.

40. The method of claim 39, wherein said polyethylene glycol has a molecular weight of about 3350.

41. The method of claim 39, wherein said polyethylene glycol is about 11.5% of said mixture.

* * * * *